United States Patent
Pardoll et al.

(10) Patent No.: US 6,193,970 B1
(45) Date of Patent: *Feb. 27, 2001

(54) CONTROLLED RELEASE OF PHARMACEUTICALLY ACTIVE SUBSTANCES FOR IMMUNOTHERAPY

(75) Inventors: Drew Pardoll, Brookeville, MD (US); Rosa Azhari, Grush Segev (IL); Kam W. Leong, Ellicott City, MD (US); Paul K Golumbe, Baltimore, MD (US); Elizabeth Jaffee, Lutherville, MD (US); Hyam Levitsky, Owings Mills, MD (US); Audrey Lazenby, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/152,918

(22) Filed: Sep. 14, 1998

Related U.S. Application Data

(63) Continuation of application No. 08/586,143, filed on Jan. 16, 1996, now Pat. No. 5,861,159, which is a continuation of application No. 08/167,562, filed on Dec. 14, 1993, now abandoned.

(51) Int. Cl.[7] ............... A61K 47/00; A61K 45/00; A61K 39/00; A61K 9/127; A61K 31/70
(52) U.S. Cl. .................. 424/184.1; 424/277.1; 424/278.1; 424/450; 424/852; 424/93.21; 514/2; 514/8; 514/44

(58) Field of Search .............. 424/184.1, 277.1, 424/278.1, 450, 852, 93.21; 514/2, 8, 44

(56) References Cited

U.S. PATENT DOCUMENTS

| | | | |
|---|---|---|---|
| 5,637,483 | * | 6/1997 | Dranoff et al. . |
| 5,759,582 | * | 6/1998 | Leong et al. . |
| 5,861,159 | * | 1/1999 | Pardoll . |
| 5,904,920 | * | 5/1999 | Dranoff et al. . |

FOREIGN PATENT DOCUMENTS

WO9816246 * 4/1998 (WO) .

OTHER PUBLICATIONS

Golumbek et al, Cancer Res. 53/24:5841–5844, 1993.*
Pardoll, Annual Rev. Immunol; 13: 399–415, 1995.*
Siemann, In: Rodent Tumor Models in Exptal Cancer Therapy Ed: Kallman Pergamon Press. NY pp. 12–15, 1987.*
Tubiana, J. Cancer Res.*

* cited by examiner

*Primary Examiner*—Nita Minnifield
(74) *Attorney, Agent, or Firm*—Shmuel Livnat; Rader Fishman & Grauer

(57) ABSTRACT

A method of stimulating a systemic immune response to a tumor cell or antigen associated with a pathogen by administering a mixture of a controlled release vehicle containing an immunopotentiating agent and antigen is described.

27 Claims, 4 Drawing Sheets

CONTROLLED RELEASE OF PHARMACEUTICALLY ACTIVE SUBSTANCES FOR IMMUNOTHERAPY

This application is a continuation of application Ser. No. 08/586,143, filed Jan. 16, 1996 (issued as U.S. Pat. 5,861, 159), which was a continuation application Ser. No. 08/167, 562, filed Dec. 14, 1993, now abandoned.

BACKGROUND OF THE INVENTION

1. Field of the Invention

This invention relates generally to the field of immunotherapy of cancer and infectious diseases, and more specifically, to a mixture of a controlled release vehicle containing an agent which potentiates the immune response to a tumor and tumor cells or specific antigens from tumors or pathogens. The invention includes a method for cancer therapy by immunization with the immunopotentiating mixture.

2. Description of Related Art

Active immunotherapy is considered to be a promising approach to the treatment and, particularly, to the inhibition of recurrences of human cancer. Specific active immunotherapy, one of the most promising approaches under investigation, involves activation of the host immune response against the tumor by immunization with tumor cells (which may be altered by mutagenesis, by treatment with a hapten, or by expression of foreign proteins) in order to activate specific effector cells of the immune system, such as cytolytic T lymphocytes. Nonspecific active immunotherapy may utilize microbial or chemical immunomodulators-to activate natural killer (NK) cells, macrophages, or lymphokine activated killing (LAK) cells. Unfortunately, much of the promise of these approaches remains unfulfilled.

One of the most critical questions in cancer immunology is why the immune system fails to eliminate tumors. In the 1970's, Hewitt articulated the notion that most tumors did not express any tumor-specific or neoantigens and, thus, could not be recognized as "foreign" by the immune system. Indeed, virtually no tumor cell surface antigens recognized by antibodies were found to be tumor specific, and furthermore, most spontaneous murine tumors were considered "poorly immunogenic" as defined by their failure to be eliminated when transferred into syngeneic hosts (Hewitt, etal., *Br. J. Cancer,* 33:241–259 1976). However, these same tumors could be rendered "immunogenic" by mutagenesis (Van Pel and Boon, *Proc. Natl. Acad. Sci. USA,* 79:4718–4722, 1982) when new antigens are expressed on the tumor cell surface.

It is possible that the immune system fails to eliminate tumors not because neoantigens are absent, but rather because the response to these neoantigens is inadequate. Therefore, a method for enhancing immunogenicity of the tumor cells so as to potentiate the host's immune response to these tumor cells would provide a key advance in immunotherapy.

Failure to respond to tumor neoantigens may be due, at least in part, to a failure of T cell help. The molecular basis for Th function is the local secretion of lymphokines, such as interleukin-2 (IL-2), that act upon CTLs whose T cell receptors have first been engaged by the appropriate antigen-MHC complex (reviewed in Möller, Immunol Rev. 51, 1980). The cytotoxic potential of NK and LAK cells is also enhanced by IL-2 (Grimm, et al, *J. Molecular and Applied Genetics,* 2:101–109, 1982; Phillips and Lanier, *J. Exp. Med.,* 164:814–825, 1986; Ortaldo, et al., *J. Exp. Med.,* 164:1193–1205,1986). Although potentiation of tumor immunity by systemic injection of interleukin 2 has been attempted, those studies were hampered by the toxicity of the systemically administered IL-2. Therefore, a method for potentiating immunity to tumors by providing accessory T cell help in the location of the tumor is a more attractive option, which has long been needed for cancer therapy.

An additional difficulty in immunotherapy results from the problems inherent in administration of a living tumor cell to a patient. In the past, tumor cells used for immunization were treated prior to immunization to reduce their proliferative potential, e.g., by irradiation or treatment with mitomycin C. Unfortunately, either one of these methods of inhibiting replication also significantly diminishes the immunogenicity of the cells. For example, it has been shown that mutagen induced variants that were irradiated with 8–10,000 Rads are no longer immunogenic (Sella, et al., *Clin. Exp. Metastasis,* 7:97–105, 1989). Similarly, murine tumor cells secreting IL-2 or IFN-γ lose their immune potential after irradiation. In addition, attempts at using membrane preparations of tumor cells also fail to produce convincing evidence of an immune response. It would therefore be advantageous to develop a means for using viable cells to induce an immunogenic response to a tumor.

A controlled delivery system which will dependably release a biologically active substance (e.g., a pharmaceutical agent) in vivo into a biological fluid (e.g., fluids of gastrointestinal tract) or into a body tissue has remained an elusive goal. Biologically active endogenous substances such as cytokines, hormones, enzymes, and antibodies are usually less stable than conventional synthetic drugs in the physiological environment. The controlled delivery system thus provides a suitable means to administer these endogenous substances to a host.

A common approach to providing controlled release of an active substance is the encapsulation of the active substance within a polymer matrix (e.g., that made of hydrophilic polymers). While some combinations of a drug and particular polymers provide a suitable drug release profile, they require a relatively large quantities of synthetic materials to be delivered to the body. This is not desirable since such materials or their metabolites may not be biocompatible in vivo or may even have toxicity such as cytotoxicity or mutagenicity. Furthermore, encapsulation involves the use of organic solvents and/or heat, both of which can be harmful to peptide or proteinaceous drugs, not to mention the above-described endogenous substances.

Complex coacervation is a process of separation of colloidal solutions into two or more immiscible liquid phases. When oppositely charged polyelectrolytes are brought into contact in aqueous medium, a spontaneous phase separation occurs with the result of formation of coacervates. The coacervate is a phase where colloids (e.g., polymers) are concentrated. Coacervation has been employed to encapsulate water insoluble biologically active substances. For example, U.S. Pat. No. 4,794,000 discloses a method for preparing a pharmaceutical composition for oral administration which is based on a two phase coacervate system where erythromycin is included as the active ingredient. U.S. Pat. No. 5,051,304 discloses microcapsules formed by coacervation between gelatin and a chemically depolymerized polysaccharide wherein a variety of water immiscible substances can be included.

While these and other references generally teach the applicability of the coacervation technique to a delivery system in the form of a coacervate, the coacervate formation to encapsulate a particular substance of interest can only be achieved by carefully controlling the phase separation conditions such as the choice and concentrations of suitable polyelectrolytes, pH and temperature.

Biodegradable polymers have become a popular in vivo sustained release drug delivery system. Therefore, the biodegradable polymer concept may be modified in order to develop a technically simpler strategy to achieve paracrine cytokine production in tumor vaccines. Based on earlier studies demonstrating the superiority of local GM-CSF production in the induction of systemic antitumor immune responses (Dranoff, et al., Proc. Nat'l. Acad. Sci., USA, 90:3539, 1993), the ability of GM-CSF incorporated into cell sized gelatin-chondroitin sulfate microspheres to act as an adjuvant when mixed with irradiated tumor cells prior to immunization is possible.

Although many vehicles for sustained release of therapeutic compounds are known, no methodology has been developed which allows a host immune system to be adequately stimulated to ameliorate not only local, but also metastatic tumors, in an animal. The present invention provides techniques which answer this need.

SUMMARY OF THE INVENTION

The present invention provides a method of stimulating a systemic immune response to a tumor cell or a specific antigen associated with a pathogen in a subject which comprises administering to the subject a composition comprising a controlled release vehicle containing an immunopotentiating agent and a tumor cell or a specific tumor or pathogen antigen. The immuno-potentiating agent is typically a cytokine such as tumor necrosis factor, GM-CSF, interleukin, and interferon.

BRIEF DESCRIPTION OF THE DRAWINGS

FIGS. 2G and 2H show GM-CSF transfectants at 7 days and 12 days, respectively. Sites were biopsied at either 7 days (FIGS. 2A, 2C, 2E) or 12 days (FIGS. 2B, 2D, 2F) after immunization and stained with hematoxylin and eosin (Magnification×400).

DETAILED DESCRIPTION OF THE INVENTION

Figure 1:
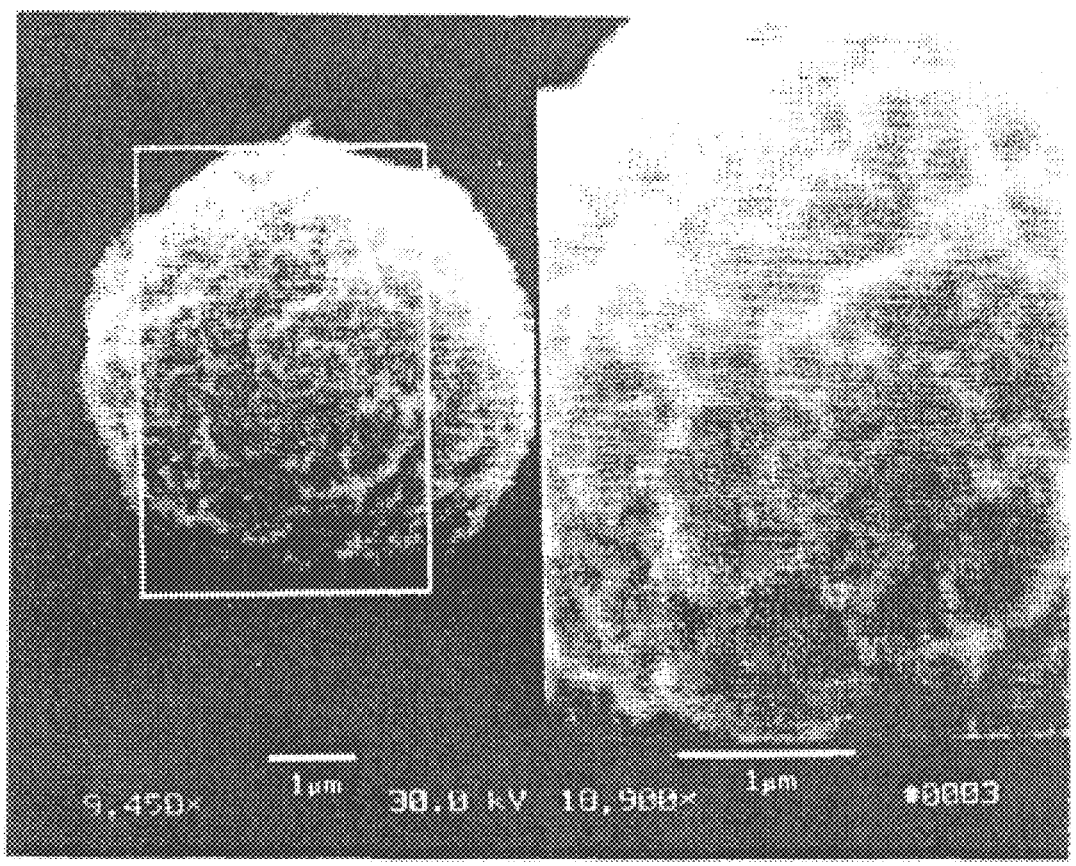
FIG. 1 is a photomicrograph of the microspheres prepared in the practice of the present invention.

In a first general embodiment, the invention provides a method for potentiating the immune response by a subject, such as man or other mammal, to a tumor antigen or antigen specifically associated with a pathogen. The potentiation of the subjects'immune response is accomplished by administering to the subject a composition which comprises an antigen, such as from tumor cells, preferably derived from the subject, and at least one immunopotentiating agent within a controlled release vehicle. Alternatively, the antigen may be virally-derived, such as a virus or virus fragment. Preferably, the immunopotentiating agent is a cytokine. Although applicants are not bound by theory, evidence suggests that the cytokine, for example, confers upon the tumor cell the ability to induce a specific immune response, probably mediated primarily by T lymphocytes. In a preferred embodiment, the vehicle is biodegradable and the antigen is whole, irradiated tumor cells derived from the subject to be treated.

Although it is not necessary for practice of the invention, various cytokine combinations may produce greatly advantageous or even synergistic effects on potentiation of immunity to the tumor. Therefore, the invention also provides that the controlled release vehicle may contain more than one immunopotentiating agent. For example, the vehicle may contain either an interleukin or an interferon or both.

The immunopotentiating agent is an agent that enhances responsiveness of the subjects' immune system to a tumor or pathogenic organism, such as a virus, present in the subject. The suitable immunopotentiating agents include agents that may not be immunogenic to the host, but nevertheless potentiate immunity by activating or enhancing the activity of cells of the immune system, such as T lymphocytes, natural killer cells, or lymphokine activated killer (LAK) cells. Included in this category of immunopotentiating agents are those encoding a number of the cytokines classified as "interleukins". These include, for example, interleukins 1 through 12. Also included in this category, although not necessarily working according to the same mechanisms, are interferons, and in particular gamma interferon (γ-IFN), tumor necrosis factor (TNF) and granulocyte-macrophage-colony stimulating factor (GM-CSF).

The method of the invention includes potentiating the immune response of a subject to a tumor or pathogen by introducing into the subject a preparation of the tumor cells or pathogen antigen described here. In a preferred embodiment, for treatment of a tumor, the cells are administered after reduction of tumor burden, e.g., by surgical resection, irradiation, chemotherapy or other appropriate techniques.

A controlled release vehicle useful as a targeted delivery system for immunopotentiating agents includes a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanical factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting tumor cells containing immunopotentiating agents in liposomes directly to the malignant tumor. A targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or $F(ab')_2$, as long as they bind efficiently to an the antigenic epitope on the target cells. Liposomes may also be targeted to cells expressing receptors for hormones or other serum factors.

The composition of the invention, comprising a controlled release vehicle containing an immunopotentiating agent and tumor cells or other antigen, can be administered parenterally by injection or by gradual perfusion over time. The tumor cells can be administered intravenously, intraperitoneally, intramuscularly, subcutaneously, intracavity, or transdermally, alone or in combination with effector cells. Preferably, administration is intradermal or subcutaneous.

Preparations for parenteral administration are contained in a "pharmaceutically acceptable carrier". Such carriers include sterile aqueous or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

Depending on the site and mode of administration of the vehicle/antigen the mixture may contain a specific cytokine. For example, when administration of vehicle/tumor cells is directly at the site of the tumor, a cytokine which directly kills cells, such as TNF, may be most effective. Alternatively, when the administration is at a distant site, a cytokine such as GM-CSF, or other molecule which can generally recruit immune cells, such as T-cells, granulocytes and macrophages, may be most effective. Those of skill in the art will be able to ascertain which cytokine to use, depending on which biological function is desired.

In a preferred embodiment, the controlled release vehicle of the invention is a biodegradable microsphere as described herein. The term "microcapsules" refers to microspheres wherein a pharmaceutically active substance is encapsulated by a coating of coacervates. Specifically useful in the present invention is a solid microsphere which is a matrix type rather than a core-shell type. If the pharmaceutically active substance is a charged molecule such as protein, the molecule is likely to participate in the complex coacervation process to form the microsphere wherein the substance is entangled with the microsphere matrix.

As applied in the present invention, the term "pharmaceutically active substance" encompasses any substance that will produce a therapeutically beneficial pharmacological response when administered to a host, including both humans and animals. More than one pharmaceutically active substance may be included, if desired, in a pharmaceutical composition used in the method of the present invention.

The pharmaceutically active substance can be employed in the present invention in various forms, such as molecular complexes or pharmaceutically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium) and the like. Furthermore, derivatives of the active substances such as esters, amides, and ethers which have desirable retention and release characteristics but which are readily hydrolyzed in vivo by physiological pH or enzymes can also be employed.

As used herein, the term "therapeutically effective amount" means that the amount of the pharmaceutically active substance is of sufficient quantity and activity to induce desired pharmacological effect which, in the present invention, is the immunopotentiation of an immune response to a tumor cell, virus, or other antigen. The amount of substance can vary greatly according to the effectiveness of a particular active substance, the age, weight, and response of the individual host as well as the nature and severity of the host's symptoms. Accordingly, there is no upper or lower critical limitation upon the amount of the active substance. The required quantity to be employed in the present invention can readily be determined by those skilled in the art.

As used herein with respect to the pharmaceutically active substance, the term "controlled release" means that the present compositions require at least an hour to release a major portion of the active substance into the surrounding medium, e.g., about 1–24 hours or even longer.

In accordance with the present invention, the pharmaceutically active substance can be encapsulated in a coacervate which, preferably, is reinforced by crosslinking. Components that may be used to form the coacervate comprise anionic and cationic molecules. By "cationic" or "anionic" molecule is meant a molecular which, under the conditions of coacervation, carries a net positive or negative charge. Many such molecules are amphoteric and contain both acidic and basic groups. Under prevailing pH conditions, these molecules can be either cationic or anionic. Cationic molecules include albumin, collagen, elastin, gelatin, and globulins. Anionic molecules include chondroitin sulfate, dermatan sulfate, heparin, heparan sulfate, hyaluronic acid, keratan sulfate, polygalacturonic acid, and polyglucuronic acid. The choice of the cationic and anionic molecules depends. on the final or intended use of the present compositions and they are expected to possess a high degree of biocompatibility. Preferably, gelatin is used as the cationic molecule in the present invention. Collagen is also preferred as the cationic molecule. Chondroitin sulfate is preferably used as the anionic molecule. Chondroitin sulfate is a mucopolysaccharide found in skeletal and soft connective tissues. The crosslinking is preferably effected by use of a gelatin-harding agent such as glutaraldehyde. Epichlorohydrin and acrolein can also be used as the crosslinking agent.

Typically, in preparing the coacervates of the present invention, both types of components are brought into contact in an aqueous medium under predetermined mixing conditions. The mixing can conveniently be carried out using equal volumes of an aqueous gelatin solution and an aqueous chondroitin sulfate solution. Preferably, gelatin is present in an aqueous solution in a concentration of from about 1% to about 10% (w/vol). Chondroitin sulfate is present in second aqueous solution in a concentration of from about 0.05% to about 2% (w/vol). Outside these concentration ranges, the formation of coacervates appears to be adversely effected.

The temperature to be employed in forming coacervates may vary somewhat with the particular method employed. Thus, a temperature from ambient temperature to about 50° C. can normally be used. However, the size of coacervates is susceptible to the temperatures of the two components when they are mixed. The higher the temperature of the gelatin solution, the smaller become the coacervates formed. The pH to be employed in forming coacervates can also vary over a fairly wide range. The yield and size of coacervates are influenced by the pH. Preferably, the pH of from about 3.5 to about 6.5 (the latter of which corresponds to the isoelectric point of gelatin) is used. The pH of the gelation solution predominates over that of the chondroitin solution in determining the pH of the mixture of the two. Optimum results in terms of both the size and yield of the coacervates are obtained at a pH of about 5.0.

The desired amount of the pharmaceutically active substance is added either to the gelatin solution or to the chondroitin sulfate solution prior to the formation of coacervates. If the active substance is water-soluble, a solution results. On the other hand, if the active substance is water-insoluble, an emulsion or suspension results.

Upon mixing of the gelatin solution and the chondroitin sulfate solution with stirring, coacervation takes place in the reaction medium to form coacervates of microspheres. Since a coacervate microsphere is generally too fragile to be isolated, crosslinking of the coacervates is necessary. The crosslinking is preferably carried out by adding to a suspension containing stabilized coacervate-coated microspheres, glutaraldehyde or another gelatin hardener. After completion of the crosslinking reaction, the resulting microspheres are recovered from the reaction medium by a conventional means, e.g., decantation, filtration, or centrifugation. The microspheres may be washed and dried in a standard technique, e.g., lyophilization.

The coacervate-coated microspheres used in the method of the present invention preferably have a sphere size (mean diameter) of about 0.5 $\mu$m to about 100 $\mu$m, and contain about 10% to 40% (w/w) of a pharmaceutically active substance. In other words, the weight ratio of the pharmaceutically active substance to the coacervate (walls) in the microspheres on a dry basis is preferably from about 1:9 to about 2:3. The pharmaceutical compositions based on the coacervate-coated microspheres can be utilized for oral ingestion, implantation, or external application to the skin or a mucous membrane. Where implantation is desired, they can be implanted subcutaneously, constitute a part of a prosthesis, or be inserted in a cavity of the human body. Subcutaneous implantation using a syringe typically consists of injecting the implant directly into subcutaneous tissue, and is a particularly effective method of controlled drug delivery. This method is viewed as an alternative to surgery where some risk may be encountered. Thus, the microcapsules obtained in the present invention can be suspended in a physiological buffer and introduced via a syringe to the desired site. For example, the present compositions incorporating a cytokine can be injected into the region of a tumor.

Upon application to the desired part of the body by the desired mode, the pharmaceutical compositions of the present invention provide controlled release of the pharmaceutically active substance by allowing it to diffuse through the coacervate walls of microspheres or by allowing the coacervate to degrade in vivo upon contact with body fluids. When the coacervate is degradable in the site (e.g., tissue) where the composition is delivered, the degree of its degradation (i.e., the release rate of the active substance) can be regulated by the degree of crosslinking of the coacervate.

The pharmaceutical microcapsule composition used in the present invention is premised primarily upon components which are found endogenous to the human body, whether natural or synthetic. The present invention thus makes it possible to employ significantly lesser quantities of non-biological materials than generally used in preparing controlled release pharmaceutical compositions. This high level of biocompatibility reflects in the absence of cytotoxicity and immunogenicity.

There are a number of potential advantages to the use of a biodegradable polymer bead strategy. First and foremost, this approach eliminates the necessity for individualized gene transfer of a cytokine. An individual's tumor cells can potentially be irradiated and mixed with the cytokine bead preparations prior to injection, thereby obviating the need for culture and transduction of the tumor cells. Also, by varying the composition and size of the cytokine bead preparations, it is possible to regulate the pharmacokinetics of local cytokine secretion such that a maximal biological effect is achieved. In the case of the GM-CSF beads specifically exemplified in this study, there was fairly rapid degradation of the beads in vivo, apparently due to increased local collagenase activity induced by the GM-CSF itself. Alterations in the composition and size of bead preparations may produce more sustained GM-subject release and will ultimately result in more effective immunization.

It is also possible to incorporate purified antigens, such as those associated with a particular pathogen or tumor, either as whole molecules or in the form of immunogenic peptides into these polymers. Such an approach is enhanced when the specific identity of the relevant antigen(s) is known. For example, papilloma virus or immunogenic antigens from this virus would be useful to treat papilloma-associated cervical cancer. The virus, viral antigen(s), either alone or in combination, would be inserted into a delivery vehicle as described herein, either alone or in combination with a cytokine.

The therapeutic mixture of vehicle/antigen used according to the method of the invention may also be administered to the subject in a delivery system, such as synthetic or natural polymers, in the form of macromolecular complexes, nanocapsules, microspheres, or beads, and lipid-based systems including oil-in-water emulsions, micelles, mixed micelles, synthetic membrane vesicles, and resealed erythrocytes. These systems are known collectively as dispersion systems. Typically, the particles comprising the system are about 20 nm–50 $\mu$m in diameter. The size of the particles allows them to be suspended in a pharmaceutical buffer and introduced to the subject using a syringe.

Materials used in the preparation of dispersion systems are typically sterilizable via filter sterilization, nontoxic, and biodegradable, such as albumin, ethylcellulose, casein, gelatin, lecithin, phospholipids, and soybean oil. Polymeric dispersion systems can be prepared by a process similar to the coacervation of microencapsulation. If desired, the density of the dispersion system can be modified by altering the specific gravity to make the dispersion hyperbaric or hypobaric. For example, the dispersion material can be made more hyperbaric by the addition of iohexol, iodixanol, metrizamide, sucrose, trehalose, glucose, or other biocompatible molecules with high specific gravity.

One type of dispersion system which can be used according to the invention consists of a dispersion of the cytokine in a polymer matrix. The therapeutic agent is released as the polymeric matrix decomposes, or biodegrades, into soluble products which are excreted from the body. Several classes of synthetic polymers, including polyesters (Pitt, et al., in *Controlled Release of Bioactive Materials,* R. Baker, Ed., Academic Press, New York, 1980); polyamides (Sidman, et aL, *Journal of Membrane Science,* 7:227, 1979); polyurethanes (Maser, et al., *Journal of Polymer Science, Polymer Symposium,* 66:259, 1979); polyorthoesters (Heller, et al., *Polymer Engineering Science,* 21:727, 1981); and polyanhydrides (Leong, et aL, *Biomaterials,* 7:364, 1986) have been studied for this purpose. Considerable research has been done on the polyesters of PLA and PLA/PGA. These polymers are readily available, since they have been used as biodegradable sutures, and they decompose into non-toxic lactic and glycolic acids (see, U.S. Pat. No. 4,578,384; U.S. Pat. No. 4,765,973; incorporated by reference).

Solid polymeric dispersion systems can be synthesized using such polymerization methods as bulk polymerization, interfacial polymerization, solution polymerization, and ring opening polymerization (Odian, G., *Principles of Polymerization,* 2nd ed., John Wiley & Sons, New York, 1981). Using any of these methods, a variety of different synthetic polymers having a broad range of mechanical, chemical, and biodegradable properties are obtained; the differences in properties and characteristics are controlled by varying the parameters of reaction temperatures, reactant concentrations, types of solvent, and reaction time. If desired, the solid polymeric dispersion system can be produced initially as a larger mass which is then ground, or otherwise processed, into particles small enough to maintain a dispersion in the appropriate physiologic buffer (see, for example, U.S. Pat. No. 4,452,025; U.S. Pat. No. 4,389,330; U.S. Pat. No. 4,696,258; incorporated by reference).

The mechanism of release of therapeutic agent from biodegradable slabs, cylinders, and spheres has been described by Hopfenberg (in *Controlled Release Polymeric Formulations,* pp. 26–32, Paul, D. R. and Harris, F. W., Eds., American Chemical Society, Washington, D.C., 1976). A simple expression additive release from these devices where release is controlled primarily by matrix degradation is:

$$M_t/M\infty = 1 - [1 - k_0 t/C_0 a]^n$$

where n=3 for a sphere, n=2 for a cylinder, and n=1 for a slab. The symbol a represents the radius of a sphere or cylinder or the half-thickness of a slab. $M_t$ and $M_\infty$ are the masses of drug release at time t and at infinity, respectively.

Another dispersion system which can be used according to the invention is a synthetic membrane vesicle. The term "synthetic membrane vesicle" denotes a structure having one or more concentric chambers, commonly known as liposomes, as well as structures having multiple non-concentric chambers bounded by a single bilayer membrane.

When phospholipids are dispersed in aqueous media, they swell, hydrate, and spontaneously form multilamellar concentric bilayer vesicles with layers of aqueous media separating the lipid bilayer. Such systems are usually referred to as multilamellar liposomes or multilamellar vesicles (MLVs) and have diameters ranging from about 100 nm to about 4 $\mu$m. When MLV's are sonicated, small unilamellar vesicles (SUVs) with diameters in the range of from about 20 nm to about 50 nm are formed, which contain an aqueous solution in the core of the SUV.

The composition of the synthetic membrane vesicle is usually a combination of phospholipids, particularly high-phase-transition-temperature phospholipids, usually in combination with steroids, especially cholesterol. Other phospholipids or other lipids may also be used.

Examples of lipids useful in synthetic membrane vesicle production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and are saturated. Illustrative phospholipids include egg phosphatidylcholine, dipalmitQylphosphatidylcholine, and distearoylphosphatidylcholine.

In preparing vesicles containing a therapeutic agent, such variables as the efficiency of drug encapsulation, lability of the drug, homogeneity and size of the resulting population of vesicles, drug-to-lipid ratio, permeability instability of the preparation, and pharmaceutical acceptability of the formulation should be considered. (Szoka, et al., *Annual Reviews of Biophysics and Bioengineering,* 9:467, 1980; Deamer, et al., in *Liposomes, Marcel Dekker,* New York, 1983, 27; Hope, et aL, *Chem. Phys. Lipids,* 40:89, 1986).

If desired, it is possible to produce synthetic membrane vesicles with various degrees of target specificity. The targeting of vesicles has been classified based on anatomical and mechanistic factors. Anatomical classification is based on the level of selectivity, for example, organ-specific, cell-specific, and organelle-specific. Mechanistic targeting can be further distinguished based upon whether it is passive or active. Passive targeting utilizes the natural tendency of vesicles to distribute to cells of the reticulo-endothelial system (RES) in organs which contain sinusoidal capillaries. Active targeting, on the other hand, involves the alteration of the vesicle by coupling the vesicle to a specific ligand such as a monoclonal antibody, sugar, glycolipid, or protein, or by changing the composition or size of the vesicles in order to achieve targeting to organs and cell types other than the naturally occurring sites of localization. Alternatively, vesicles may physically localize in capillary beds.

Another dispersion system which can be used according to the invention is resealed erythrocytes. When erythrocytes are suspended in a hypotonic medium, swelling occurs and the cell membrane ruptures. As a consequence, pores are formed with diameters of approximately 200–500 Å which allow equilibration of the intracellular and extracellular environment. If the ionic strength of this surrounding media is then adjusted to isotonic conditions and the cells incubated at 37° C., the pores will close such that the erythrocyte reseals. This technique can be utilized to entrap the therapeutic agent inside the resealed erythrocyte.

The following non-limiting examples are provided to further illustrate the present invention.

EXAMPLE 1

Encapsulation of GM-CSF

In this example, the following reagents and solvent were used: Gelatin (type A, 60 bloom; Sigma, St. Louis, Mo.), chondroitin-4-sulfate (Sigma), glutaraldehyde (Sigma), collagenase (type VII; Sigma), fluorescein isothiocyanate (FITC; Sigma), 2,2'-azino-di-[3-ethyl benzthioazoline-6-sulfonic acid] (ABTS; Bio-Rad, Hercules, Calif.), and sheep red blood cells (Thomas D. Morris, Inc., Philadelphia, Pa.).

Formation of γ-IFN or GM-CSF microspheres: Gelatin (porcine, type A, 60 bloom), chondroitin-4-sulfate, albumin (bovine), and glutaraldehyde were purchased from Sigma. Bloom number is an indication of the strength of the gel. The higher the Bloom number, the stronger the gel. Type A is derived from acid-cured tissue. All of the reagents used were of analytical grade. Centricon 10 filters were purchased from Amicon, USA. A 5% gelatin solution and distilled water was prepared and maintained at 37° C. One mg of lyophilized γ-IFN was dissolved in 5 ml of 0.2% chondroitin sulfate solution in distilled water at room temperature. Coacervation was achieved by rapidly adding 5 ml of gelatin solution to 5 ml of the stirred chondroitin sulfate solution. The microspheres were cross-linked by addition of 50 µl of 25% glutaraldehyde solution to the microsphere suspension. After 30 min, 6 ml of ethanolamine—HCl, pH 8.0 was added to stop the cross-linking reaction and the quench the excess aldehyde groups on the microspheres. The microspheres were then washed with PBS and isolated by centrifugation. GM-CSF loaded microspheres were prepared in a similar manner, except the GM-CSF concentration in chondroitin sulfate solution was 600 µg/ml. Blank microspheres were prepared in an identical manner, but in the absence of cytokines.

The amount of GM-CSF encapsulated in the microspheres was determined by analysis in solution before and after encapsulation. The analysis was conducted according to ELISA (Genzyme).

EXAMPLE 2 in vivo Treatment of Tumor Cells Using Cytokine Encapsulated Microspheres

Microspheres of the invention were prepared which contained γ-IFN or GM-CSF. These microspheres were then administered in combination with tumor cells to vaccinate animals to the tumor. The animals were then studied for tumor progression. The vaccination scheme resulted in a systemic antitumor response comparable to GM-CSF gene-transduced tumor vaccines.

Tumor Models: B16–F10 melanoma cells were maintained in Dulbecco's Modified Eagles medium containing 10% fetal calf serum and penicillin/streptomycin. Animals used were 6–12 weeks old C57BL6 females obtained from the Jackson Laboratories. B16 cells were transduced with the GM-CSF gene using the MFG retroviral vector (Dranoff, et al., supra). Murine GM-CSF levels were tested using FDCP-1 (ATCC, Rockville, Md.) cells as a biological assay.

Vaccinations: Cultured tumor monolayers were treated with trypsin, washed once in medium containing serum and washed twice in HBSS before injection. Tumor cells received 5000 rads from a $^{137}$Cs source discharging 132 rads/min.

Histology: Tumors for histologic examination were fixed in 10% ethyl buffered formalin, processed in paraffin embedment and stained with hemotoxylin and eosin.

Experimental studies using murine tumor models have demonstrated that potent systemic immunity can be generated using tumor vaccines engineered by gene transfer to secrete certain cytokines. The underlying physiologic principle behind these strategies involved the sustained release of high doses of cytokine at the site of the tumor. In some cases, this paracrine approach appears to enhance tumor antigen presentation and avoids systemic cytokine toxicity. The widespread clinical use of autologous cytokine gene transduced tumor vaccines may be limited by the technical difficulty and labor intensity of individualized gene transfer. In the example herein, high doses of GM-CSF encapsulated in cell-sized gelatin—chondroitin sulfate microspheres were mixed with irradiated tumor cells prior to subcutaneous injection. This vaccination scheme resulted in systemic antitumor immune responses comparable to GM-CSF gene transduced tumor vaccines.

Three different types of microspheres were prepared for studies: 1) Control microspheres containing no cytokine; 2) microspheres containing GM-CSF; and 3) microspheres containing γ-interferon. Vaccinations were done by mixing 1×10⁶ beads with 1×10⁶ tumor cells in 1 ml HBSS and injected immediately after mixing. The B16–F10 murine melanoma model was used. This is a murine melanoma arising in and passagable in the C57BL6 mouse strain. This model demonstrates a poorly immunogenic tumor in which vaccination with irradiated wild-type cells produces relatively little protective immunity against challenge with live wild-type tumor cells at a distant site. Previous analysis with this model indicated that B16–F10 cells transduced with a gene encoding GM-CSF generated potent systemic immunity against challenge with wild-type tumor cells. In contrast, B16–F10 cells transduced with most other cytokine genes, such as γ-IFN, do not generate enhanced systemic immune responses against challenge with wild-type tumors (Dranoff, et.al., *Proc. Natl'; Acad. Sci. U.S.A.* 90:3539, 1993).

Histologic analysis of the vaccine sites revealed striking differences among the different bead preparations, indicating differential in vivo bioactivity of the released cytokines (FIG. 2). When control beads (not containing incorporated cytokine) were used, numerous tumor cells were present at seven days post-injection, interspersed with abundant numbers of microspheres. The microspheres were seen as variably sized round eosinophilic bodies that appeared to lie free in the tissue. Interspersed with the tumor and microspheres, there was an inflammatory infiltrate, which consisted predominantly of lymphocytes, but also contained numerous eosinophils and mono-cytes/macrophages. At 12 days post-injection, numerous microspheres were still present, but there were few tumor cells (FIG. 2B). An inflammatory infiltrate persisted, but the inflammatory response was somewhat decreased with lesser numbers of lymphocytes.

Figure 2A:
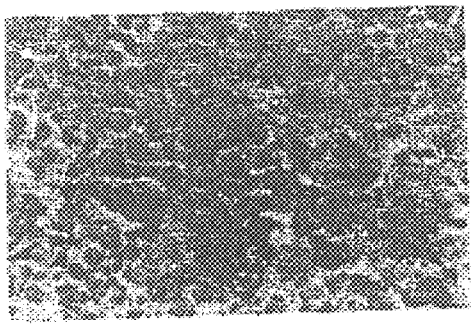
FIGS. 2A–2H show the histology of immunization sites from B16F10 melanoma mixed with gelatin/chondroitin sulfate beads. C57BL6 mice were immunized subcutaneously with $1 \times 10^6$ irradiated B16–F10 melanoma cells admixed with $1 \times 10^6$ gelatin/chondroitin sulfate microspheres containing either nothing (control) (FIGS. 2A, 2B) γ-IFN (FIGS. 2C, 2D), or GM-CSF (FIGS. 2E, 2F).
Figure 2B:
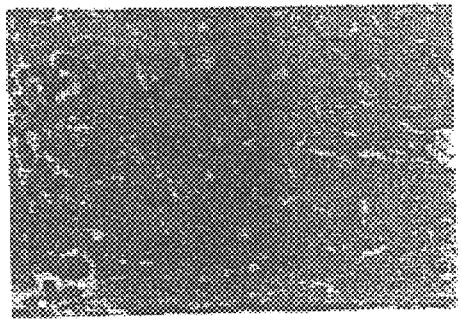
Figure 2C:
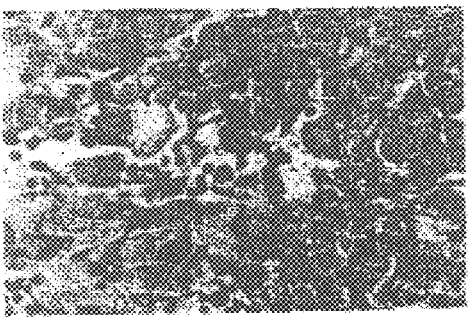
Figure 2D:
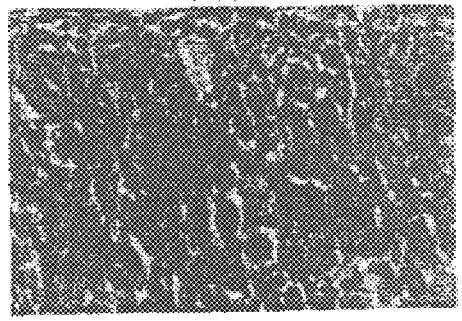

When γ-interferon microspheres were used at the vaccine site, both tumor cells and beads were numerous at 7 days post-injection (FIG. 2C). While most of the microspheres appeared to lie free within tissue, scattered microspheres were present within the cytoplasm of macrophages. An inflammatory infiltrate was present, but it was less intense and patchy than that seen with the GM-CSF bead preparation (see below). The predominant cell type in the inflammatory infiltrate was eosinophils. At 12 days post-injection numerous microspheres persisted, the tumor cells were few in number and the inflammatory infiltrate was only mild (FIG. 2D).

Figure 2E:
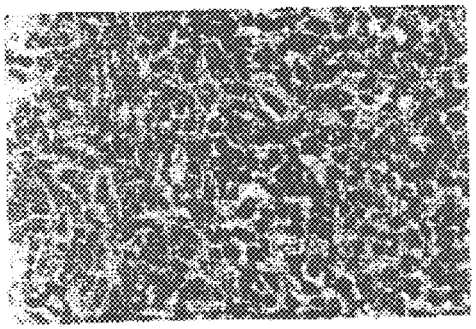
Figure 2F:
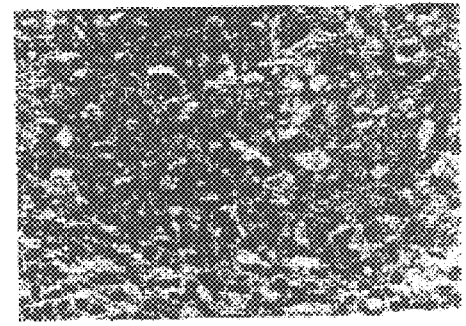
Figure 2G:
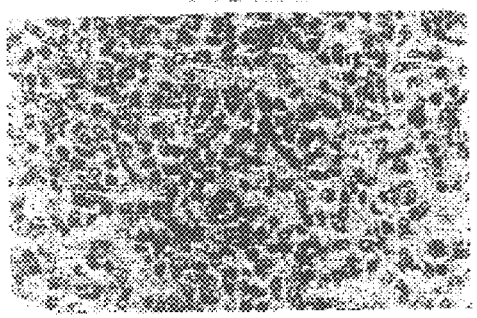
Figure 2H:
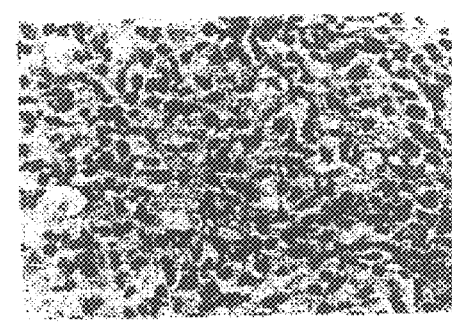

With the GM-CSF microspheres, tumor cells were present, but only rare small microsphere remnants were detected at 7 days post-injection (FIG. 2E). An intense inflammatory infiltrate was admixed with the tumor cells, consisting of numerous eosinophils and monocytes/macrophages with somewhat lesser numbers of lymphocytes. At 12 days post-injection, no microspheres were detected and tumor cells were few (FIG. 2F). A moderate inflammatory infiltrate persisted. The significantly greater rapidity of microsphere degradation in vivo seen when GM-CSF was incorporated suggests a feed forward process in which GM-CSF initially released from the beads attracts and activates inflammatory cells (probably granulocytes and monocytes/macrophages) which, in turn, produce extracellular enzymes capable of more rapidly degrading the collagen/chondroitin sulfate microsphere matrix. This more rapid degradation likely results in an increased rate of local GM-CSF delivery, thereby amplifying the process.

Figure 3A:
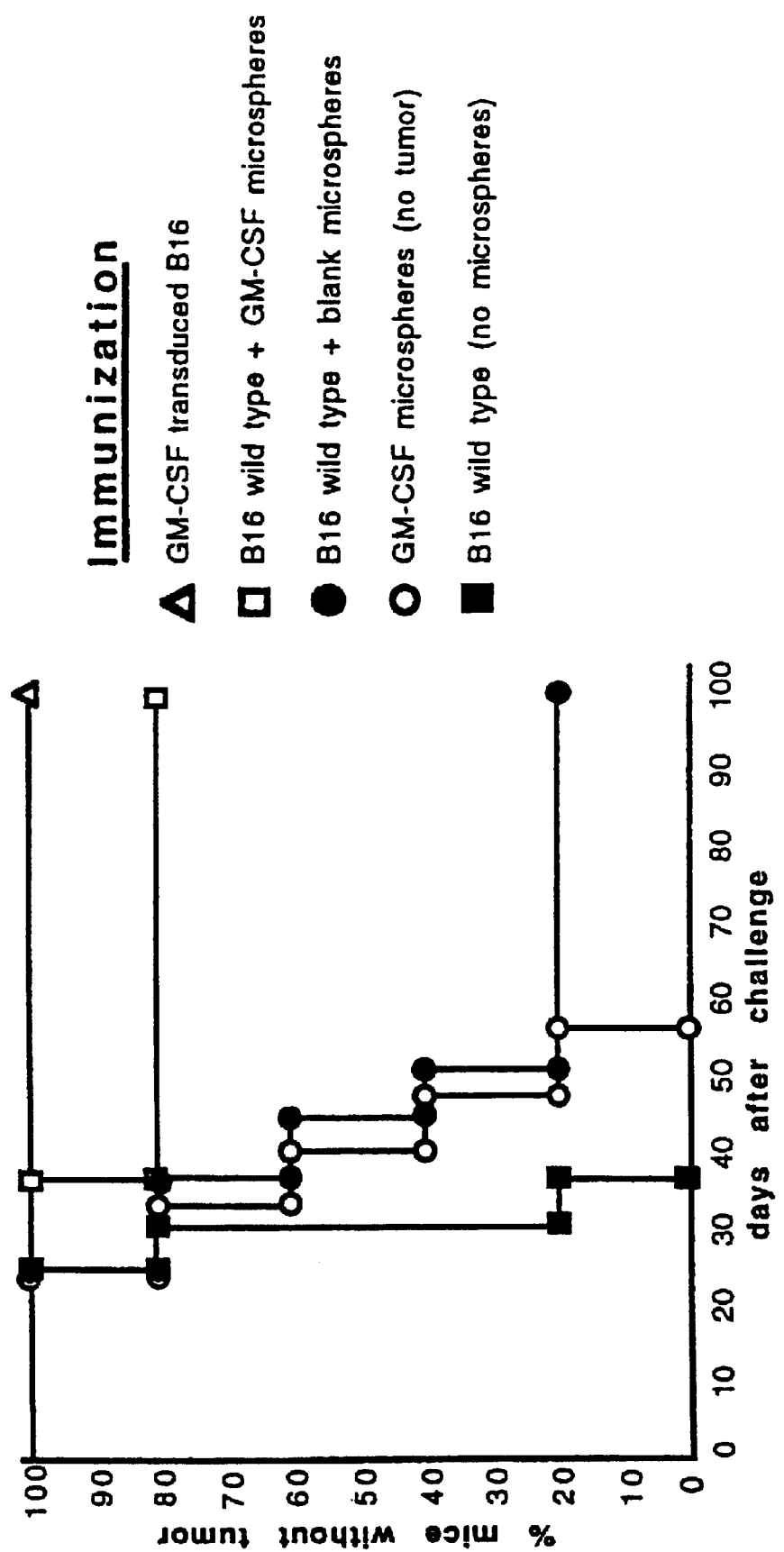
FIG. 3A shows C57BL6 mice immunized subcutaneously in the left flank with either nothing, $1 \times 10^6$ irradiated B16–F10 melanoma cells alone (■), $1 \times 10^6$ irradiated B16–FT melanoma cells+$1 \times 10^6$ gelatin/chondroitin sulfate microspheres containing GM-CSF (□), $1 \times 10^6$ irradiated B16 WT melanoma cells+$1 \times 10^6$ gelatin/chondroitin sulfate microspheres not containing any GM-CSF.

In order to determine whether the local release of GM-CSF by this microsphere preparation resulted in enhanced systemic antitumor immunity, vaccinated animals were challenged 2 weeks later on the opposite flank with $1 \times 10^5$ live wild-type B16 melanoma cells. FIG. 3A shows C57BL6 mice immunized subcutaneously in the left flank with either nothing, $1 \times 10^6$ irradiated B16–F10 melanoma cells alone (■), $1 \times 10^6$ irradiated B16FT melanoma cells+ $1 \times 10^6$ gelatin/chondroitin sulfate microspheres containing GM-CSF (□), $1 \times 10^6$ irradiated B16 WT melanoma cells+ $1 \times 10^6$ gelatin/chondroitin sulfate microspheres not containing any GM-CSF (•), $1 \times 10^6$ gelatin/chondroitin sulfate microspheres containing GM-CSF (no B16–F10 cells) (○) or $1 \times 10^6$ irradiated B16–F10 melanoma cells transduced with the murine GM-CSF gene (Δ). Mice were challenged 2 weeks later in the right flank with $1 \times 10^5$ live B16WT cells and tumor growth was assessed twice/week.

Figure 3B:
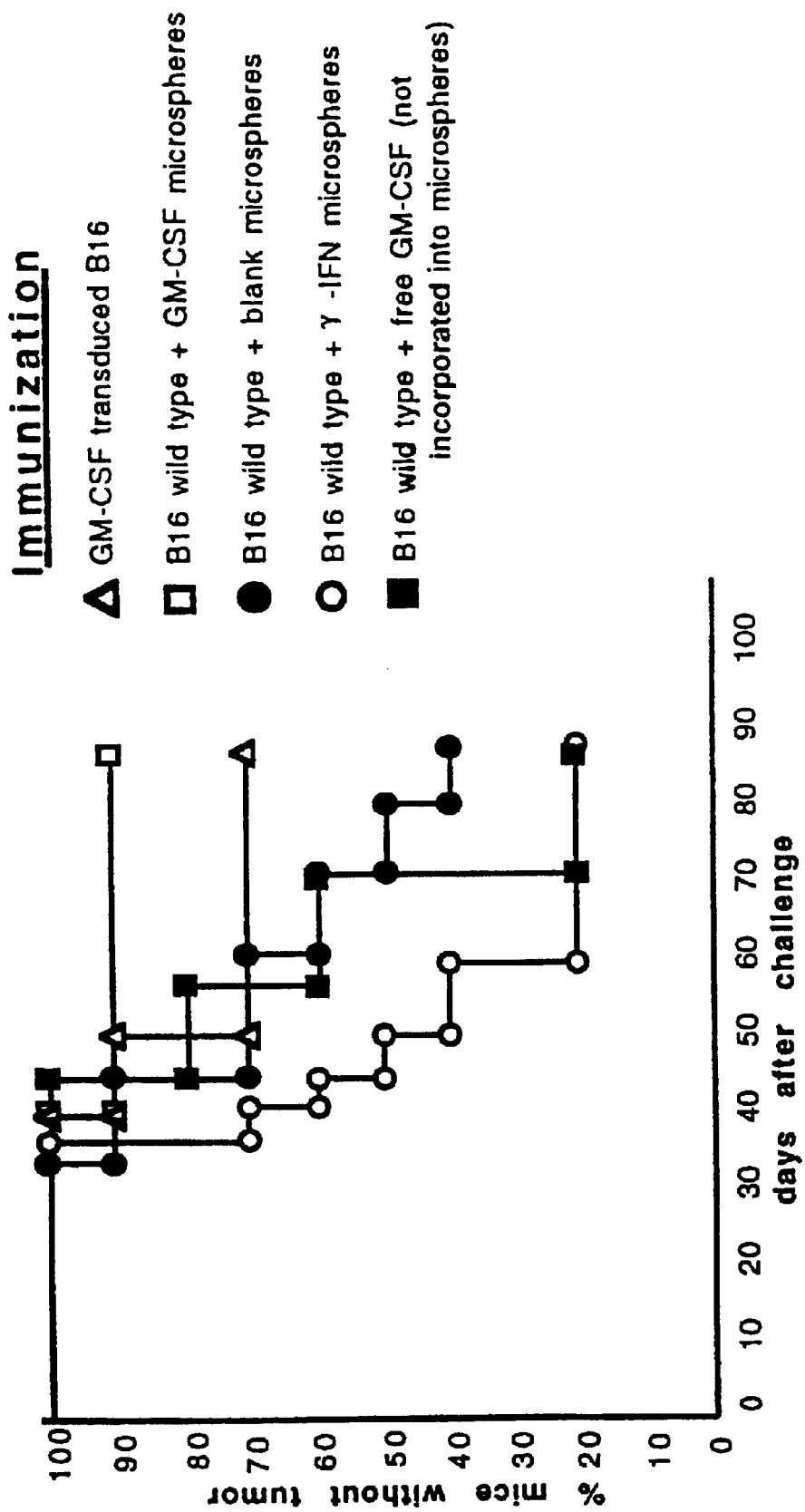
FIG. 3B shows the experiment as in FIG. 3A but with additional immunization groups of $1 \times 10^6$ irradiated B16WT melanoma cells+$1 \times 10^6$ gelatin/chrondroitin sulfate microspheres containing γ-IFN (O) and $1 \times 10^6$ irradiated B16WT melanoma cells mixed with 1 mg of free GM-CSF (not incorporated into microspheres) (■) prior to injection. Each group contained 10 mice. Tumor growth was assessed twice/week by palpation.

FIG. 3 demonstrates that the GM-CSF microsphere preparation admixed with the B16–F10 tumor cells generated comparable systemic immunity against challenge with wild-type tumor cells. This effect required the presence of both GM-CSF containing microspheres and tumor cells. Immunization with GM-CSF containing microspheres in the absence of (FIG. 3A; ○), or at a different site from, the tumor cells did not generate an antitumor immune response. In addition, immunization with tumor cells mixed with γ-interferon containing microspheres (FIG. 3B; ○) failed to generate significant systemic protective responses. It therefore appears that the specificity of cytokine effect is similar between the microsphere release preparation and directly transduced tumor cells. Interestingly, mixture of irradiated tumor cells with blank (non-cytokine incorporated) microsphere generated a level of systemic antitumor response that was greater than background although significantly less than when GM-CSF is incorporated. Finally, when irradiated tumor cells were mixed with a high dose of free (non-microsphere incorporated) GM-CSF, no significant systemic protective responses were seen (FIG. 3B; ■). These results demonstrate the importance of sustained local release of GM-CSF afforded by incorporation into the biodegradable microspheres.

These results provide evidence that biodegradable microspheres with encapsulated cytokines can be utilized as a strategy for paracrine cytokine delivery in tumor vaccine development.

The invention now being fully described, it will be apparent to one of ordinary skill in the art that many changes and modifications can be made without departing from the spirit or scope of the invention.

What is claimed is:

1. A method of potentiating a local inflammatory or immune response to the administration of a tumor antigen in a mammalian subject, which local response results in systemic immunity to the antigen in the subject, comprising administering to a local site in the subject
   (a) the tumor antigen in the form of tumor cells, or subcellular antigenic material thereof, and;
   (b) a cytokine or cytokines in a controlled release vehicle, which cytokine or cytokines stimulate T cell responses, such that the cytokine or cytokines is or are released from the controlled release vehicle in a paracrine-like manner and potentiate the generation of the local response that leads to the systemic immunity.

2. A method of providing an immunopotentiating cytokine or cytokines in a paracrine-like manner in the vicinity of locally-administered tumor antigen in a mammalian subject to promote the local generation of an inflammatory and immune response that results in a state of systemic immunity to the antigen, said method comprising
   administering to a local site in the subject the cytokine or cytokines in a controlled release vehicle, and the tumor antigen in the form of tumor cells or subcellular antigenic material, such that controlled release of the cytokine in a paracrine-like manner in physical proximity with the tumor antigen promotes the local generation of said response and results in the state of systemic immunity.

3. The method of claim 1 or 2 wherein the local site is an intramuscular site, a subcutaneous site, an intradermal site or an intracranial site.

4. The method of claim 1 or 2, wherein the tumor antigen or tumor cell is derived from the subject to whom said cytokine and said tumor antigen is being administered.

5. The method of claim 1 or 2 wherein the tumor antigen and the cytokine or cytokines are combined in the controlled release vehicle.

6. The method of claim 1 or 2 wherein said cytokine or cytokines comprise at least two cytokines.

7. The method of claim 1 or 2, wherein the cytokine or cytokines is selected from the group consisting of tumor necrosis factor, GM-CSF, an interleukin and an interferon.

8. The method of claim 1 or 2, wherein the mammalian subject is a human.

9. The method of claim 1 or 2 wherein the tumor antigen is selected from the group consisting of a melanoma antigen, an adenocarcinoma antigen, a leukemia antigen, a lymphoma antigen and a sarcoma antigen.

10. The method of claim 1 or 2, wherein the tumor antigen is in the form of tumor cells.

11. The method of claim 10, wherein the tumor cells are selected from the group consisting of melanoma cells, adenocarcinoma cells, leukemia cells, lymphoma cells and sarcoma cells.

12. The method of claim 1 or 2 wherein the controlled release vehicle comprises a dispersion system that is a colloidal dispersion system, a polymeric dispersion system or a synthetic membrane vesicle.

13. The method of claim 12 wherein the controlled release vehicle is a biodegradable dispersion system.

14. The method of claim 12 wherein the dispersion system is selected from the group consisting of macromolecular complexes, nanocapsules, microspheres, beads, oil-in-water emulsions, micelles, mixed micelles, liposomes and resealed erythrocytes.

15. The method of claim 13, wherein the biodegradable dispersion system is made from a substance selected from the group consisting of (a) albumin, (b) ethylcellulose, (c) casein, (d) gelatin, (e) lecithin, (f) phospholipid (g) soybean oil and (h) a mixture of any of (a)–(g).

16. A pharmaceutical composition that, when administered to a mammalian subject, potentiates a local inflammatory or immune response to a tumor antigen in the subject, which local response results in systemic immunity to the antigen, which composition comprises:

(a) at least one immunopotentiating cytokine in a controlled release vehicle;

(b) a tumor antigen in the form of tumor cells or subcellular antigenic material, optionally in said controlled release vehicle; and (c) a pharmaceutically acceptable carrier.

17. A pharmaceutical composition that provides an immunopotentiating cytokine or cytokines for paracrine-like delivery, in the vicinity of locally-administered tumor antigen, to a mammalian subject, comprising:

(a) an immunopotentiating cytokine or cytokines in a controlled release vehicle;

(b) a tumor antigen in the form of tumor cells or subcellular antigenic material, optionally in said controlled release vehicle; and (c) a pharmaceutically acceptable carrier.

18. The composition of claim 16 or 17, wherein the tumor antigen and the cytokine or cytokines are combined in said controlled release vehicle.

19. The composition of claim 16 or 17 wherein said cytokines are at least two cytokines.

20. The composition of claim 16 or 17 wherein the cytokine or cytokines is or are selected from the group consisting of tumor necrosis factor, GM-CSF, an interleukin, and an interferon.

21. The composition of claim 16 or 17, wherein the tumor antigen or tumor cell is derived from the same subject to whom said composition is to be administered.

22. The composition of claim 16 or 17, wherein the tumor antigen or tumor cell is selected from the group consisting of a melanoma antigen or cell, an adenocarcinoma antigen or cell, a leukemia antigen or cell, a lymphoma antigen or cell and a sarcoma antigen or cell.

23. The composition of claim 16 or 17, wherein the controlled release vehicle comprises a dispersion system that is a colloidal dispersion system, a polymeric dispersion system or a synthetic membrane vesicle.

24. The composition of claim 23, wherein the dispersion system is a biodegradable dispersion system.

25. The composition of claim 23 wherein the dispersion system selected from the group consisting of macromolecular complexes, nanocapsules, microspheres, beads, oil-in-water emulsions, micelles, mixed micelles, liposomes and resealed erythrocytes.

26. The composition of claim 24, wherein the biodegradable dispersion system is made from a substance selected from the group consisting of (a) albumin, (b) ethylcellulose, (c) casein, (d) gelatin, (e) lecithin, (f) phospholipid (g) soybean oil and (h) a mixture of any of (a)–(g).

27. A method for paracrine-like delivery of a cytokine or cytokines to a local site of tumor immunization in a subject, comprising administering to a local site of tumor immunization at least one immunopotentiating cytokine in a controlled release vehicle, wherein said tumor immunization is with tumor antigen-bearing tumor cells or subcellular materials thereof, such that the cytokine or cytokines is or are released in a time-controlled manner in said site, thereby achieving said paracrine-like delivery.

\* \* \* \* \*